United States Patent [19]
MacCoss et al.

[11] Patent Number: 6,124,319
[45] Date of Patent: Sep. 26, 2000

[54] 3,3-DISUBSTITUTED PIPERIDINES AS MODULATORS OF CHEMOKINE RECEPTOR ACTIVITY

[75] Inventors: Malcolm MacCoss, Freehold; Sander G. Mills, Scotch Plains, both of N.J.

[73] Assignee: Merck & Co., Inc., Rahway, N.J.

[21] Appl. No.: 09/009,488

[22] Filed: Jan. 20, 1998

Related U.S. Application Data

[60] Provisional application No. 60/035,854, Jan. 21, 1997.

[51] Int. Cl.⁷ ...................... A61K 31/395; A61K 31/415; A61K 31/505; A61K 31/40; A61K 31/55
[52] U.S. Cl. .......................... 514/318; 514/210; 514/385; 514/256; 514/422; 514/212.01; 514/218
[58] Field of Search ..................................... 514/210, 385, 514/256, 422, 318, 212.01, 218

[56] References Cited

U.S. PATENT DOCUMENTS

| | | | |
|---|---|---|---|
| 5,340,822 | 8/1994 | Edmonds-Alt et al. | 514/316 |
| 5,350,852 | 9/1994 | Edmonds-Alt et al. | 544/336 |
| 5,434,158 | 7/1995 | Shah | 514/278 |
| 5,559,132 | 9/1996 | Miller | 514/329 |
| 5,589,489 | 12/1996 | Shenvi et al. | 514/323 |
| 5,635,510 | 6/1997 | Burkholder et al. | 514/278 |
| 5,807,856 | 9/1998 | Bock et al. | |

FOREIGN PATENT DOCUMENTS

| | | | |
|---|---|---|---|
| 0 673 928 | 3/1995 | European Pat. Off. | C07D 211/52 |
| 0 714 891 | 6/1996 | European Pat. Off. | C07D 211/58 |
| WO 97/10211 | 3/1997 | WIPO | C07D 211/32 |

OTHER PUBLICATIONS

Edmods–Alt et al 125CA:195439, 1995.
Giardina et al, J. Med. Chem. vol. 39 (12) pp. 2281–84, 1996.
Chem. abstr. vol. 124, Abstract No. 124:53407, Loetscher et al. 'Activation of NK cells . . . ' 1996.
Chem.abstr. vol. 125, Abstract No. 125:299098, Napolitano et al. 'Molecular cloning of TERI . . . ' 1996.

Primary Examiner—Russell Travers
Attorney, Agent, or Firm—J. Eric Thies; David L. Rose

[57] ABSTRACT

The present invention is directed to 3,3-disubstituted piperidines of the formula I:

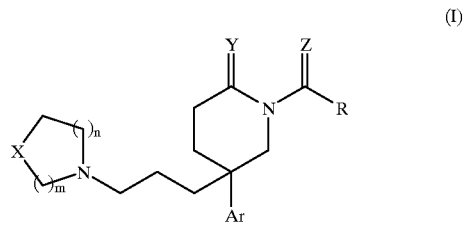

(wherein X, Y, Z, Ar, R, m and n are defined herein) which are useful as modulators of chemokine receptor activity. In particular, these compounds are useful as modulators of the chemokine receptors CCR-1, CCR-2, CCR-2A, CCR-2B, CCR-3, CCR-4, CCR-5, CXCR-3, and/or CXCR-4.

10 Claims, No Drawings

3,3-DISUBSTITUTED PIPERIDINES AS MODULATORS OF CHEMOKINE RECEPTOR ACTIVITY

CROSS REFERENCE TO RELATED APPLICATIONS

This application claims priority under 35 U.S.C. § 119(e) from U.S. application Ser. No. 60/035,854, filed Jan. 21, 1997.

BACKGROUND OF THE INVENTION

Chemokines are chemotactic cytokines that are released by a wide variety of cells to attract macrophages, T cells, eosinophils, basophils and neutrophils to sites of inflammation (reviewed in Schall, Cytokine, 3, 165–183 (1991) and Murphy, Rev. Immun. 12, 593–633 (1994)). There are two classes of chemokines, C—X—C ($\alpha$) and C—C ($\beta$), depending on whether the first two cysteines are separated by a single amino acid (C—X—C) or are adjacent (C—C). The $\alpha$-chemokines, such as interleukin-8 (IL-8), neutrophil-activating protein-2 (NAP-2) and melanoma growth stimulatory activity protein (MGSA) are chemotactic primarily for neutrophils, whereas $\beta$-chemokines, such as RANTES, MIP-1$\alpha$, MIP-1$\beta$, monocyte chemotactic protein-1 (MCP-1), MCP-2, MCP-3 and eotaxin are chemotactic for macrophages, T-cells, eosinophils and basophils (Deng, et al., Nature, 381, 661–666 (1996)).

The chemokines bind specific cell-surface receptors belonging to the family of G-protein-coupled seven-transmembrane-domain proteins (reviewed in Horuk, Trends Pharm. Sci., 15, 159–165 (1994)) which are termed "chemokine receptors." On binding their cognate ligands, chemokine receptors transduce an intracellular signal though the associated trimeric G protein, resulting in a rapid increase in intracellular calcium concentration. There are at least seven human chemokine receptors that bind or respond to $\beta$-chemokines with the following characteristic pattern: CCR-1 (or "CKR-1" or "CC-CKR-1") [MIP-1$\alpha$, MIP-1$\beta$, MCP-3, RANTES] (Ben-Barruch, et al., J. Biol. Chem., 270, 22123–22128 (1995); Beote, et al, Cell, 72, 415–425 (1993)); CCR-2A and CCR-2B (or "CKR-2A"/"CKR-2A" or "CC-CKR-2A"/"CC-CKR-2A") [MCP-1, MCP-3, MCP-4]; CCR-3 (or "CKR-3" or "CC-CKR3") [eotaxin, RANTES, MCP-3] (Combadiere, et al., J. Biol. Chem., 270, 16491–16494 (1995); CCR-4 (or "CKR-4" or "CC-CKR-4") [MIP-1$\alpha$, RANTES, MCP-1] (Power, et al., J. Biol. Chem. 270, 19495–19500 (1995)); CCR-5 (or "CKR-5" or "CC-CKR-5") [MIP-1$\alpha$, RANTES, MIP-1$\beta$] (Sanson, et al., Biochemistry, 35, 3362–3367 (1996)); and the Duffy blood-group antigen [RANTES, MCP-1] (Chaudhun, et al., J. Biol. Chem., 269, 7835–7838 (1994)). The $\beta$-chemokines include eotaxin, MIP ("macrophage inflammatory protein"), MCP ("monocyte chemoattractant protein") and RANTES ("regulation-upon-activation, normal T expressed and secreted").

Chemokine receptors, such as CCR-1, CCR-2, CCR-2A, CCR-2B, CCR-3, CCR-4, CCR-5, CXCR-3, CXCR-4, have been implicated as being important mediators of inflammatory and immunoregulatory disorders and diseases, including asthma and allergic diseases, as well as autoimmune pathologies such as rheumatoid arthritis and atherosclerosis. For example, the chemokine receptor CCR-3 plays a pivotal role in attracting eosinophils to sites of allergic inflammation. Accordingly, agents which modulate chemokine receptors would be useful in such disorders and diseases.

A retrovirus designated human immunodeficiency virus (HIV-1) is the etiological agent of the complex disease that includes progressive destruction of the immune system (acquired immune deficiency syndrome; AIDS) and degeneration of the central and peripheral nervous system. This virus was previously known as LAV, HTLV-III, or ARV.

Certain compounds have been demonstrated to inhibit the replication of HIV, including soluble CD4 protein and synthetic derivatives (Smith, et al., Science, 238, 1704–1707 (1987)), dextran sulfate, the dyes Direct Yellow 50, Evans Blue, and certain azo dyes (U.S. Pat. No. 5,468,469). Some of these antiviral agents have been shown to act by blocking the binding of gp120, the coat protein of HIV, to its target, the CD4 gyycoprotein of the cell.

Entry of HIV-1 into a target cell requires cell-surface CD4 and additional host cell cofactors. Fusin has been identified as a cofactor required for infection with virus adapted for growth in transformed T-cells, however, fbsin does not promote entry of macrophagetropic viruses which are believed to be the key pathogenic strains of HIV in vivo. It has recently been recognized that for efficient entry into target cells, human immunodeficiency viruses require the chemokine receptors CCR-5 and CXCR-4, as well as the primary receptor CD4 (Levy, N. Engl. J. Med., 335(20), 1528–1530 (Nov. 14 1996). The principal cofactor for entry mediated by the envelope glycoproteins of primary macrophage-trophic strains of HIV-1 is CCR5, a receptor for the $\beta$-chemokines RANTES, MIP-1$\alpha$ and MIP-1$\beta$ (Deng, et al., Nature 381, 661–666 (1996)). HIV attaches to the CD4 molecule on cells through a region of its envelope protein, gp120. It is believed that the CD-4 binding site on the gp120 of HIV interacts with the CD4 molecule on the cell surface, and undergoes conformational changes which allow it to bind to another cell-surface receptor, such as CCR5 and/or CXCR-4. This brings the viral envelope closer to the cell surface and allows interaction between gp41 on the viral envelope and a fusion domain on the cell surface, fusion with the cell membrane, and entry of the viral core into the cell. Macrophage-tropic HIV and SIV envelope proteins have been shown to induce a signal through CCR-5 on CD4+ cells resulting in chemotaxis of T cells which may enhance the replication of the virus (Weissman, et al., Nature, 389, 981–985 (1997)). It has been shown that $\beta$-chemokine ligands prevent HIV-1 from fusing with the cell (Dragic, et al., Nature, 381, 667–673 (1996)). It has further been demonstrated that a complex of gp120 and soluble CD4 interacts specifically with CCR-5 and inhibits the binding of the natural CCR-5 ligands MIP-1$\alpha$ and MIP-1$\beta$ (Wu, et al., Nature, 384, 179–183 (1996); Trkola, et al., Nature, 384, 184–187 (1996)).

Humans who are homozygous for mutant CCR-5 receptors which do not serve as co-receptors for HIV-1 in vitro apper to be unusually resistant to HIV-1 infection and are not immunocompromised by the presence of this genetic variant (Nature, 382, 722–725 (1996)). Similarly, an alteration in the CCR-2 gene, CCR2-641, can prevent the onset of full-blown AIDS (Smith, et al., Science, 277, 959–965 (1997). Absence of CCR-5 appears to confer protection from HIV-1 infection (Nature, 382, 668–669 (1996)). An inherited mutation in the gene for CCR5, Delta 32, has been shown to abolish functional expression of the gene and individuals homozygous for the mutation are apparently not susceptible to HIV infection. Other chemokine receptors may be used by some strains of HIV-1 or may be favored by non-sexual routes of transmission. Although most HIV-1 isolates studied to date utilize CCR-5 or fusin, some can use both as well as the related CCR-2B and CCR-3 as co-receptors (Nature Medicine, 2(11), 1240–1243 (1996)). Nevertheless, drugs targeting chemokine receptors may not be unduly compromised by the genetic diversity of HIV-1 (Zhang, et al., *Nature,* 383, 768 (1996)). The β-chemokine macrophage-derived chemokine (MDC) has been shown to inhibit HIV-1 infection (Pal, et al., *Science,* 278 (5338), 695–698 (1997). The chemokines RANTES, MIP-1α, MIP-1β, vMIP-I, vMIP-II, SDF-1 have also been shown to suppress HIV. A derivative of RANTES, (AOP)-RANTES, is a subnanomolar antagonist of CCR-5 function in monocytes (Simmons, et al., *Science,* 276, 276–279 (1997)). Monoclonal antibodies to CCR-5 have been reported to block infection of cells by HIV in vitro. Accordingly, an agent which could block chemokine receptors in humans who possess normal chemokine receptors should prevent infection in healthy individuals and slow or halt viral progression in infected patients (see *Science,* 275, 1261–1264 (1997)). By focusing on the host's cellular immune response to HIV infection, better therapies towards all subtypes of HIV may be provided. These results indicate that inhibition of chemokine receptors presents a viable method for the prevention or treatment of infection by HIV and the prevention or treatment of AIDS.

The peptides eotaxin, RANTES, MIP-1-60 , MIP-1β, MCP-1, and MCP-3 are known to bind to chemokine receptors. As noted above, the inhibitors of HIV-1 replication present in supernatants of CD8+ T cells have been characterized as the β-chemokines RANTES, MIP-1α and MIP-1β. U.S. Pat. Nos. 5,340,822, 5,350,852, 5,434,158, 5,559,132, 5,589,489, and 5,635,510 and PCT Patent Publication WO 95/05377 disclose certain compounds as tachykinin antagonists. EPO Patent Publications EP 0 512 901 (published Nov. 11, 1992), EP 0 673 928 (published Sep. 27, 1995) and EP 0 723 959 (published Jul. 31, 1996) disclose certain piperidines as tachykinin antagonists. A poster presentation by T. Harrison, et al. (Gordon Conference on Medicinal Chemistry, Colby Sawyer College, New London, N.H., Aug. 4–9, 1996) disclosed certain 3,3-disubstituted piperidines as tachykinin antagonists.

SUMMARY OF THE INVENTION

The present invention is directed to compounds which are modulators of chemokine receptor activity and are useful in the prevention or treatment of certain inflammatory and immunoregulatory disorders and diseases, including asthma and allergic diseases, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

The present invention is further concerned with compounds which inhibit the entry of human immunodeficiency virus (HIV) into target cells and are of value in the prevention of infection by HIV, the treatment of infection by HIV and the prevention and/or treatment of the resulting acquired immune deficiency syndrome (AIDS). The present invention also relates to pharmaceutical compositions containing the compounds and to a method of use of the present compounds and other agents for the prevention and treatment of AIDS and viral infection by HIV.

DETAILED DESCRIPTION OF THE INVENTION

The present invention is directed to a compound of formula I:

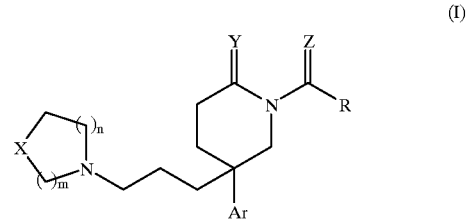

wherein:
m is zero, 1 or 2;
n is 1, 2 or 3, with the proviso that the sum of m+n is 1 to 4;
X is:

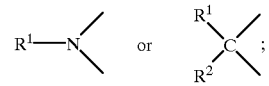

one of Y and Z is =O whereas the other represents two hydrogen atoms;
Ar is selected from the group consisting of:
unsubstituted phenyl;
phenyl which is substituted by 1, 2 or 3 substituents selected from: hydroxy, cyano, halogen, trifluoromethyl, $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, and $C_{1-6}$alkoxy; thienyl; benzothienyl; naphthyl; unsubstituted indolyl; and indolyl which is substituted on the nitrogen atom by a $C_{1-4}$alkyl group;
R is selected from the group consisting of:
unsubstituted phenyl; and
phenyl substituted by 1, 2 or 3 substituents selected from: hydroxy, cyano, halogen, trifluoromethyl, $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, and $C_{1-6}$alkoxy;
$R^1$ is selected from the group consisting of:
hydrogen; $C_{1-6}$alkyl;
$C_{1-6}$alkyl substituted by 1 or 2 substituents selected from: hydroxy, —$OR^3$, oxo, —$NHCOR^3$, —$NR^3R^4$, cyano, halogen, trifluoromethyl, unsubstituted phenyl, and phenyl substituted by 1 or 2 substituents selected from: hydroxy, cyano, halogen and trifluoromethyl;
unsubstituted phenyl;
phenyl substituted by 1, 2 or 3 substituents selected from: hydroxy, cyano, —$C(O)NR^3R^4$, —$NR^3R^4$, —$NR^3COR^4$, halogen, trifluoromethyl, $C_{1-4}$alkyl, —$S(O)_pC_{1-4}$alkyl and —$C(O)R^3$;
unsubstituted aryl;
aryl substituted by 1, 2 or 3 substituents selected from: hydroxy, cyano, —$C(O)NR^3R^4$, —$NR^3R^4$, —$NR^3COR^4$, halogen, trifluoromethyl, $C_{1-4}$alkyl, —$S(O)_pC_{1-4}$alkyl and —$C(O)R^3$; and
a saturated heterocyclic ring of 4, 5 or 6 ring atoms which ring contains 1 or 2 nitrogen atoms, one of which may be at the point of attachment to the remainder of the molecule, and optionally containing in the ring an oxygen atom, which ring is substituted on any available nitrogen atom by a group $R^5$ and which ring may be further substituted by a group selected from: hydroxy$C_{1-4}$alkyl, $C_{1-4}$alkoxy$C_{1-4}$alkoxy, oxo and $COR^3$, and which ring may have fused thereto a phenyl ring, wherein the phenyl ring may be substituted by 1 or 2 substituents selected from: hydroxy, cyano, —C(O)NR$^3$R$^4$, —NR$^3$R$^4$, —NR$^3$COR$^4$, halogen, trifluoromethyl, $C_{1-4}$alkyl, —S(O)$_p$C$_{1-4}$alkyl, and —C(O)R$^3$;

$R^2$ is selected from:

$C_{1-6}$alkyl hydroxy$C_{1-6}$alkyl, hydroxy, OR$^3$, halogen, trifluoromethyl, nitro, cyano, —NR$^3$R$^4$, —NHCOR$^3$, NR$^3$COR$^4$, —NH$^3$COR$^3$, —NR$^3$CO$_{2R}$$^4$, —NHS(O)$_p$R$^3$, NR$^3$, NR$^3$S(O)$_p$R$^4$, —CONR$^3$R$^4$, —COR$^3$, —CO$_2$R$^3$ and —S(O)$_p$R$^3$;

or R$^1$ and R$^2$ are joined together to form a 5- or 6-membered nonaromatic ring which may contain in the ring 1 or 2 groups of the formula —NR$^5$—, which ring is optionally substituted by an oxo group and which ring may be substituted by, or have fused thereto, a phenyl group, wherein the phenyl ring may be substituted by 1 or 2 substituents selected from: hydroxy, cyano, —C(O)NR$^3$R$^4$, —NR$^3$R$^4$, —NR$^3$COR$^4$, halogen, trifluoromethyl, $C_{1-4}$alkyl, —S(O)$_p$C$_{1-4}$alkyl, and —C(O)R$^3$;

R$^3$ and R$^4$ are each independently selected from:

hydrogen;

unsubstituted $C_{1-6}$alkyl;

$C_{1-6}$alkyl substituted by 1 or 2 substituents selected from unsubstituted: phenyl, hydroxy, oxo, cyano, $C_{1-4}$alkoxy and trifluoromethyl;

$C_{1-6}$alkoxy;

unsubstituted phenyl; and phenyl substituted by 1, 2 or 3 substituents selected from: hydroxy, $C_{1-4}$alkyl, cyano, halogen, and trifluoromethyl;

or the group —NR$^3$R$^4$ is a saturated or partially saturated heterocyclic ring of 4 to 7 ring atoms, which ring may optionally contain in the ring one oxygen or sulfur atom or a group selected from: —NR$^5$—, —S(O)— or —S(O)$_2$— and which ring may be optionally substituted by one or two groups selected from: hydroxy$C_{1-4}$alkyl, $C_{1-4}$alkoxy$C_{1-4}$alkyl, oxo, —COR$^6$ and —CO$_2$R$^6$;

R$^5$ is selected from:

hydrogen, $C_{1-4}$alkyl, —S(O)$_2$C$_{1-4}$alkyl, —C(O)R$^3$, unsubstituted phenyl and benzyl;

R$^6$ is selected from: hydrogen or $C_{1-4}$alkyl; and p is zero, 1 or 2;

or a pharmaceutically acceptable salt thereof.

When used herein the term "halogen" means fluorine, chlorine, bromine and iodine. The preferred halogen are fluorine and chlorine of which fluorine is most preferred.

When used herein the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

The term "alkenyl" as a group or part of a group means that the group is straight or branched and contains at least one double bond. Examples of suitable alkenyl groups include vinyl and allyl.

The term "alkynyl" as a group or part of a group means that the group is straight or branched and contains at least one triple bond. An example of a suitable alkynyl group is propargyl.

Suitable cycloalkyl and cycloalkyl-alkyl groups include cyclopropyl, cyclobutyl, cyclopentyl, cyclohexyl, cyclopropylmethyl and cyclobutylmethyl.

When used herein the term "heteroaryl" represents a heteroaromatic ring including furanyl, thienyl, pyrrolyl, oxazolyl, thiazolyl, isoxazolyl, isothiazolyl, imidazolyl, pyrazolyl, triazolyl, oxadiazolyl, thiadiazolyl, tetrazolyl, pyridyl, pyrazinyl, pyrimidyl, benzofuranyl, benzthienyl, indolyl, benzimidazolyl, benzoxazolyl and quinolyl.

Where the group NR$^3$R$^4$ forms a saturated heterocylic ring of 4 to 7 ring atoms which may optionally contain in the ring one oxygen or sulfur atom or a group selected from —NR$^5$—, —S(O)— or —S(O)$_2$—, suitable heterocylic groups include azetidinyl, pyrrolidino, piperidino, homopiperidino, piperazino, N-methylpiperazino, morpholino and thiomorpholino.

Suitable substituents on the saturated heterocyclic ring include —CH$_2$OH, —CH$_2$OCH$_3$, oxo, —CHO, —CO$_2$H, —CO$_2$CH$_3$, and —CO$_2$CH$_2$CH$_3$.

Preferred compounds of the present invention include those compounds of formula I, with the exception of:

5-[3-{4,4-(N-sulfonamidomethyl-3,3-indolyl)piperidino}propyl]-5-[3,4-diphenyl]-1-benzylpiperidin-2-one;

5-[3-{4-(2-keto-1-benzimidazolinyl)-piperidino}propyl]-5-[3,4-dichlorophenyl]-1-benzylpiperidin-2-one;

5-[3-{4-acetyl-4-phenyl-piperidino}propyl]-5-[3,4-dichlorophenyl]-1-benzylpiperidin-2-one;

5-[3-{1-phenyl-1,3,8-triazaspiro[4.5]decan-4-one}propyl]-5-[3,4-dichlorophenyl]-1-benzylpiperidin-2-one;

5-[3-{4,4-(N-sulfonamidomethyl-3,3-indolyl)piperidino}propyl]-5-[3,4-diphenyl]-1-benzoylpiperidine;

5-[3-{4-(2-keto-1-benzimidazolinyl)-piperidino}propyl]-5-[3,4-dichlorophenyl]-1-benzoylpiperidine;

5-[3-{4-acetyl-4-phenyl-piperidino}propyl]-5-[3,4-dichlorophenyl]-1-benzoylpiperidine;

5-[3-{1-phenyl-1,3,8-triazaspiro[4.5]decan-4-one}propyl]-5-[3,4-dichlorophenyl]-1-benzoylpiperidine; and 5-[3-{4,4-(1,1-indanyl)piperidino}propyl]-5-[3,4-diphenyl]-1-benzoylpiperidine.

A preferred class of compounds of formula I for use in the present invention is that wherein the sum of m+n is 3. In particular, m is preferably 2. In particular, n is preferably 1.

A preferred group of compounds for use in the present invention is wherein X is:

wherein R$^1$ and R$^2$ are defined above.

Ar preferably represents unsubstituted phenyl or phenyl substituted by 1, 2 or 3 substituents selected from: hydroxy, cyano, halogen, triflouromethyl, $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, and $C_{1-6}$alkoxy. Preferred substituents are halogen atoms, most especially chlorine atoms. In particular, Ar represents phenyl substituted by two substituents. Preferably Ar represents a 3,4-disubstituted phenyl ring.

R preferably represents unsubstituted phenyl or phenyl substituted by 1, 2 or 3 substituents selected from: hydroxy, cyano, halogen, trifluoromethyl, $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, and $C_{1-6}$alkoxy. Preferred substituents are halogen atoms, most especially chlorine atoms. In particular, R represents an unsubstituted phenyl ring.

R$^1$ preferably represents an unsubstituted phenyl group or a saturated heterocyclic ring of 5 ring atoms which ring contains 1 or 2 nitrogen atoms, one of which is at the point of attachment to the remainder of the molecule, which ring is substituted on any available nitrogen atom by a group $R^5$, preferably where $R^5$ is hydrogen, and which ring is preferably substituted by an oxo group, and which ring has fused thereto a phenyl ring, wherein the phenyl ring may be substituted by 1 or 2 substituents selected from: hydroxy, cyano, —C(O)NR$^3$R$^4$, —NR$^3$R$^4$, —NR$^3$COR$^4$, halogen, trifluoromethyl, $C_{1-4}$alkyl, —S(O)$_p$C$_{1-4}$alkyl, and —C(O)R$^3$. Preferably the phenyl ring is unsubstituted.

$R^2$ preferably represents hydrogen or —COR$^3$, where $R^3$ represents $C_{1-6}$alkyl, in particular $C_{1-3}$alkyl, especially methyl.

A further preferred class of compound of formula I for use in the present invention is that wherein $R^1$ and $R^2$ are joined together to form a 5-membered non-aromatic ring which may contain in the ring 1 or 2 groups of the formula NR$^5$, which ring is optionally substituted by an oxo group and which ring may be substituted by, or have fused thereto, a phenyl group, wherein the phenyl ring may be substituted by 1 or 2 substituents selected from: hydroxy, cyano, —C(O)NR$^3$R$^4$, —NR$^3$R$^4$, —NR$^3$COR$^4$, halogen, trifluoromethyl, $C_{1-4}$alkyl, —S(O)$_p$C$_{1-4}$alkyl, and —C(O)R$^3$. Preferably the phenyl ring, where present, is unsubstituted.

Where present, $R^3$ and $R^4$ each independently preferably represent hydrogen or $C_{1-6}$alkyl.

$R^5$ preferably represents hydrogen, $C_{1-4}$alkyl, —S(O)$_2$C$_{1-4}$alkyl or unsubstituted phenyl. In particular, $R^5$ is preferably hydrogen, —S(O)$_2$CH$_3$ or phenyl.

From the foregoing, it will be appreciated that a particularly preferred sub-group of compounds for use in the present invention include are those of formula (Ia):

(Ia)

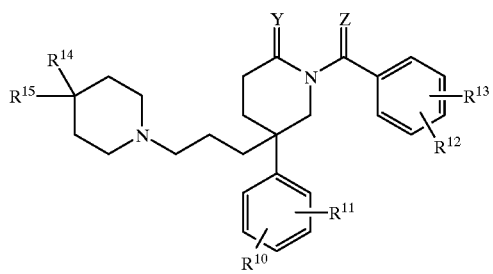

wherein:
$R^{10}$, $R^{11}$, $R^{12}$ and $R^{13}$ are selected from: hydrogen and halogen;
$R^{14}$ is an unsubstituted phenyl group or a saturated heterocyclic ring of 5 ring atoms which ring contains 1 or 2 nitrogen atoms, one of which is at the point of attachment to the remainder of the molecule, which ring is substituted on any available nitrogen atom by a group $R^5$, and which ring may be substituted by an oxo group, and which ring has fused thereto a phenyl ring, wherein the phenyl ring may be substituted by 1 or 2 substituents selected from: hydroxy, cyano, —C(O)NR$^3$R$^4$, —NR$^3$R$^4$, —NR$^3$COR$^4$, halogen, trifluoromethyl, $C_{1-4}$alkyl, —S(O)$_p$C$_{1-4}$alkyl, and —C(O)R$^3$;
$R^{15}$ is —COR$^3$, where $R^3$ is $C_{1-6}$alkyl;
or $R^{14}$ and $R^{15}$ are joined together to form a 5-membered non-aromatic ring which may contain in the ring 1 or 2 groups of the formula NR$^5$, which ring is optionally substituted by an oxo group and which ring may be substituted by, or have fused thereto, a phenyl group, wherein the phenyl ring may be substituted by 1 or 2 substituents selected from: hydroxy, cyano, —C(O)NR$^3$R$^4$, —NR$^3$R$^4$, —NR$^3$COR$^4$, halogen, trifluoromethyl, $C_{1-4}$alkyl, —S(O)$_p$C$_{1-4}$alkyl, and —C(O)R$^3$; and one of Y and Z is =O whereas the other represents two hydrogen atoms; or a pharmaceutically acceptable salt thereof.

A preferred class of compound of formula (Ia) for use in the present invention is that wherein:
$R^{10}$ and $R^{11}$ each are chlorine;
$R^{12}$ and $R^{13}$ each are hydrogen;
$R^{14}$ is unsubstituted phenyl;
$R^{15}$ is —COCH$_3$;
or $R^{14}$ and $R^{15}$ are joined together to form a 5-membered non-aromatic ring which may contain in the ring 1 or 2 groups of the formula —NR$^5$—, which ring is optionally substituted by an oxo group and which ring may be substituted by, or have fused thereto, an unsubstituted phenyl group, wherein $R^5$ is selected from: hydrogen, —S(O)$_2$CH$_3$ and phenyl.

Particularly preferred compounds of formula I for use in the present invention are those wherein:
m is 2, n is 1 and X is:

to give a group of the formula:

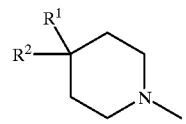

of which preferred examples are selected from:

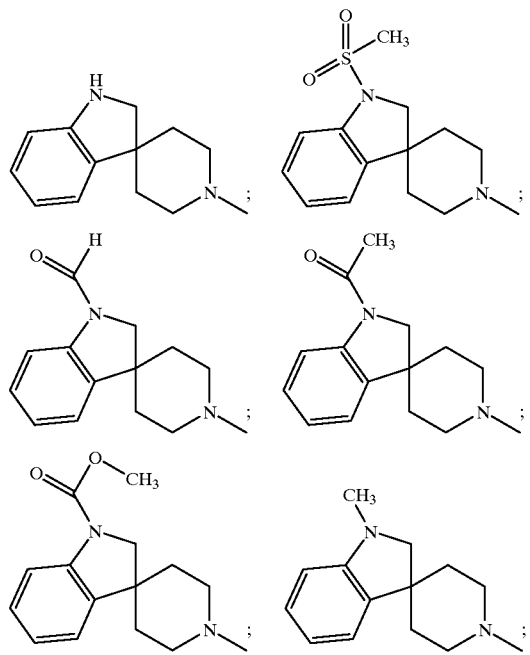

wherein each phenyl ring may be substituted by 1 or 2 substituents selected from:

hydroxy, cyano, —C(O)NR³R⁴, —NR³R⁴, —NR³COR⁴, halogen, trifluoromethyl, C$_{1-4}$alkyl, —S(O)$_p$C$_{1-4}$alkyl and —C(O)R³, where R³, R⁴ and p are as previously defined above.

Particularly preferred examples of groups for the compounds of use in the present invention which are represented by include:

Exemplifying the present invention is the use of a compound selected from the group consisting of:

5-[3-{4,4-(N-sulfonamidomethyl-3,3-indolyl)piperidino}propyl]-5-[3,4-diphenyl]-1-benzylpiperidin-2-one;

5-[3-{4-(2-keto-1-benzimidazolinyl)-piperidino}propyl]-5-[3,4-dichlorophenyl]-1-benzylpiperidin-2-one;

5-[3-{4-acetyl-4-phenyl-piperidino}propyl]-5-[3,4-dichlorophenyl]-1-benzylpiperidin-2-one;

5-[3-{1-phenyl-1,3,8-triazaspiro[4.5]decan-4-one}propyl]-5-[3,4-dichlorophenyl]-1-benzylpiperidin-2-one;

5-[3-{4,4-(N-sulfonamidomethyl-3,3-indolyl) piperidino}propyl]-5-[3,4-diphenyl]-1-benzoylpiperidine;

5-[3-{4-(2-keto-1-benzimidazolinyl)-piperidino}propyl]-5-[3,4-dichlorophenyl]-1-benzoylpiperidine;

5-[3-{4-acetyl-4-phenyl-piperidino}propyl]-5-[3,4-dichlorophenyl]-1-benzoylpiperidine;

5-[3-{1-phenyl-1,3,8-triazaspiro[4.5]decan-4-one}propyl]-5-[3,4-dichlorophenyl]-1-benzoylpiperidine;

5-[3-{4,4-(1,1-indanyl)piperidino}propyl]-5-[3,4-diphenyl]-1-benzoylpiperidine;

and pharmaceutically acceptable salts thereof.

For use in medicine, the salts of the compounds of formula I will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts such as those formed with hydrochloric acid, fumaric acid, p-toluenesulphonic acid, maleic acid, succinic acid, acetic acid, citric acid, tartaric acid, carbonic acid or phosphoric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The pharmaceutically acceptable salts of the present invention may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope solvates of the compounds of formula I and salts thereof, for example, hydrates.

The compounds according to the invention may have one or more asymmetric centres, and may accordingly exist both as enantiomers and as diastereoisomers. It is to be understood that all such isomers and mixtures thereof are encompassed within the scope of the present invention.

The subject compounds are useful in a method of modulating chemokine receptor activity in a patient in need of such modulation comprising the administration of an effective amount of the compound. Exemplifying the invention is the use of the compounds disclosed in the Examples and elsewhere herein.

The present invention is directed to the use of the foregoing compounds as modulators of chemokine receptor activity. In particular, these compounds are useful as modulators of the chemokine receptors, including CCR-1, CCR-2, CCR-2A, CCR-2B, CCR-3, CCR-4, CCR-5, CXCR-3, and/or CXCR-4.

The present invention is further directed to the use of compounds of this general structure which are disclosed as being antagonists of neurokinin receptors. Such compounds are disclosed, for example, in: U.S. Pat. No. 5,317,020; U.S. Pat. No. 5,340,822; U.S. Pat. No. 5,350,852; U.S. Pat. No. 5,411,971; U.S. Pat. No. 5,434,158; U.S. Pat. No. 5,446,052; U.S. Pat. No. 5,534,525; U.S. Pat. No. 5,559,132; U.S. Pat. No. 5,560,700; U.S. Pat. No. 5,589,489; U.S. Pat. No. 5,635,510; EP 0 512 901 , Nov. 11, 1992; EP 0 59 040, Apr. 6, 1994; EP 0 673 928, Sep. 27, 1995; EP 0 698 601, Feb. 28, 1996; EP 0 625 509, Nov. 23, 1994; EP 0 630 887, Dec. 28, 1994; EP 0 680 962, Nov. 8, 1995; EP 0 709 37, May 1, 1996; EP 0 709 376, May 1, 1996; EP 0 723 959, Jul. 31, 1996; EP 0 739 891; WO 94/10146, May 11, 1994; WO 94/11045, Aug. 4, 1994; WO 94/26735, Nov. 24, 1994; WO 94/29309, Dec. 22, 1994; WO 95/05377, Feb. 23, 1995; WO 95/12577, May 11, 1995; WO 95/15961, Jun. 15, 1995; WO 95/16682, Jun. 22, 1995; WO 95/21187; WO 95/26335, Oct. 5, 1995; WO 95/26338, Oct. 5, 1995; WO 95/35279; WO 96/06094, Feb. 29, 1996; WO 96/10568, Apr. 11, 1996; WO 96/23787, Aug. 8, 1996; WO 96/24582, Aug. 15, 1996; WO 96/28441; and WO 96/32385. Accordingly, the present invention embraces the use of a compound disclosed in these publications as a modulator of chemokine receptor activity.

The utility of the compounds in accordance with the present invention as modulators of chemokine receptor activity may be demonstrated by methodology known in the art, such as the assay for CCR-1 and/or CCR-5 binding as disclosed by Van Riper, et al., *J. Exp. Med.,* 177, 851–856 (1993), and the assay for CCR-2 and/or CCR-3 binding as disclosed by Daugherty, et al., *J. Exp. Med.,* 183 2349–2354 (1996). Cell lines for expressing the receptor of interest include those naturally expressing the receptor, such as EOL-3 or THP-1, or a cell engineered to express a recombinant receptor, such as CHO, RBL-2H3, HEK-293. For example, a CCR3 transfected AML14.3D10 cell line has been placed on restricted deposit with American Type Culture Collection in Rockville, Md. as ATCC No. CRL-12079, on Apr. 5, 1996. The utility of the compounds in accordance with the present invention as inhibitors of the spread of HIV infection in cells may be demonstrated by methodology known in the art, such as the HIV quantitation assay disclosed by Nunberg, et al., *J. Virology,* 65 (9), 4887–4892 (1991).

In particular, the compounds of the following examples had activity in binding to either the CCR-5 receptor or the CCR-3 receptor in the aforementioned assays. Such a result is indicative of the intrinsic activity of the compounds in use as modulators of chemokine receptor activity.

Mammalian chemokine receptors provide a target for interfering with or promoting eosinophil and/or lymphocyte function in a mammal, such as a human. Compounds which inhibit or promote chemokine receptor function, are particularly useful for modulating eosinophil and/or lymphocyte function for therapeutic purposes. Accordingly, the present invention is directed to compounds which are useful in the prevention and/or treatment of a wide variety of inflammatory and immunoregulatory disorders and diseases, including asthma and allergic diseases, as well as autoimmune pathologies such as rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited. For example, eosinophilic infiltration to inflammatory sites (e.g., in asthma) can be inhibited according to the present method.

Similarly, an instant compound which promotes one or more functions of a mammalian chemokine receptor (e.g., a human chemokine) is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes. For example, eosinophils can be recruited to combat parasitic infections.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the method of the present invention. In a preferred embodiment, the disease or condition is one in which the actions of eosinophils and/or lymphocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersentitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with promoters of chemokine receptor function, include, but are not limited to: immunosuppression, such as that in individuals with immunodeficiency syndromes such as AIDS, individuals undergoing radiation therapy, chemotherapy, therapy for autoimmune disease or other drug therapy (e.g., corticosteroid therapy), which causes immunosuppression; immunosuppression due congenital deficiency in receptor function or other causes; and infectious diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, Taeniasis saginata, Cysticercosis); visceral worms, visceral larva migrans (e.g., Toxocara), eosinophilic gastroenteritis (e.g., Anisaki spp., Phocanema ssp.), cutaneous larva migrans (*Ancylostona braziliense, Ancylostoma caninum*).

The compounds of the present invention are accordingly useful in the prevention and treatment of a wide variety of inflammatory and immunoregulatory disorders and diseases.

In another aspect, the instant invention may be used to evaluate putative specific agonists or antagonists of chemokine receptors, including CCR-1, CCR-2, CCR-2A, CCR-2B, CCR-3, CCR-4, CCR-5, CXCR-3, and CXCR-4. Accordingly, the present invention is directed to the use of these compounds in the preparation and execution of screening assays for compounds which modulate the activity of chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the chemokine receptors, including CCR-1, CCR-2, CCR-2A, CCR-2B, CCR-3, CCR-4, CCR-5, CXCR-3, and CXCR-4. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating chemokine receptor activity in humans and animals comprising combining a compound of the present invention with a pharmaceutical carrier or diluent.

The present invention is further directed to the use of these compounds in the prevention or treatment of infection by a retrovirus, in particular, the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery. In addition, a compound of the present invention may be used for the prevention of infection by HIV and the prevention of AIDS, such as in post-coital prophylaxis or in the prevention of maternal transmission of the HIV virus to a fetus or a child upon birth.

In a preferred aspect of the present invention, a subject compound may be used in a method of inhibiting the binding of a human immunodeficiency virus to a chemokine receptor, such as CCR-5 and/or CXCR-4, of a target cell, which comprises contacting the target cell with an amount of the compound which is effective at inhibiting the binding of the virus to the chemokine receptor.

The subject treated in the methods above is a mammal, preferably a human being, male or female, in whom modulation of chemokine receptor activity is desired. "Modulation" as used herein is intended to encompass antagonism, agonism, partial antagonism and/or partial agonism. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

Combined therapy to modulate chemokine receptor activity and thereby prevent and treat inflammatory and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities.

For example, in the treatment or prevention of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compounds of the pressent invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) VLA-4 antagonists such as those described in U.S. Pat. No. 5,510,332, WO97/03094, WO97/02289, WO96/40781, WO96/22966, WO96/20216, WO96/01644, WO96/06108, WO95/15973 and WO96/31206; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CCR-1, CCR-2, CCR-3 and CCR-5; (j) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), α-glucosidase inhibitors (acarbose) and glitazones (troglitazone and pioglitazone); (l) preparations of interferon beta (interferon beta-1α, interferon beta-1β); (m) other compounds such as 5-aminosalicylic acid and prodrugs thereof, antimetabolites such as azathioprine and 6-mercaptopurine, and cytotoxic cancer chemotherapeutic agents. The weight ratio of the compound of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

The present invention is further directed to combinations of the present compounds with one or more agents useful in the prevention or treatment of AIDS. For example, the compounds of this invention may be effectively administered, whether at periods of pre-exposure and/or post-exposure, in combination with effective amounts of the AIDS antivirals, immunomodulators, anti-infectives, or vaccines known to those of ordinary skill in the art.

ANTIVIRALS

| Drug Name | Manufacturer | Indication |
| --- | --- | --- |
| 097 | Hoechst/Bayer | HIV infection, AIDS, ARC (non-nucleoside reverse transcriptase (RT) inhibitor) |
| 141 W94 | Glaxo Wellcome | HIV infection, AIDS, ARC (protease inhibitor) |
| 1592U89 | Glaxo Wellcome | HIV infection, AIDS, ARC (protease inhibitor) |
| Abacavir (1592U89) | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which neutralizes pH labile alpha aberrant Interferon | Advanced Biotherapy Concepts (Rockville, MD) | AIDS, ARC |
| AR177 | Aronex Pharm | HIV infection, AIDS, ARC |
| beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infection, AIDS, ARC (protease inhibitor) |
| (−) 6-Chloro-4(S)-cyclopropylethynyl-4(S)-trifluoro-methyl-1,4-dihydro-2H-3,1-benzoxazin-2-one | Merck | HIV infection, AIDS, ARC (non-nucleoside reverse transcriptase inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus immune globin | MedImmune | CMV retinitis |
| Cytovene Ganciclovir | Syntex | sight threatening CMV peripheral CMV retinitis |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |

-continued

| | | |
| --- | --- | --- |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-266 | DuPont-Merck Pharmaceuticals | HIV infection, AIDS, ARC (non-nucleoside reverse transcriptase inhibitor) |
| DMP-450 | AVID (Camden, NJ) | HIV infection, AIDS, ARC (protease inhibitor) |
| Efavirenz (DMP 266) | DuPont Merck | HIV infection, AIDS, ARC (non-nucleoside RT inhibitor) |
| EL10 | Elan Corp, PLC (Gainesville, GA) | HIV infection |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| GW 141 | Glaxo Welcome | HIV infection, AIDS, ARC (protease inhibitor) |
| GW 1592 | Glaxo Welcome | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc | CMV retinitis, HIV infection, other CMV infections |
| PNU-140690 | Pharmacia Upjohn | HIV infection, AIDS, ARC (protease inhibitor) |

-continued

| Drug Name | Manufacturer | Indication |
|---|---|---|
| Probucol | Vyrex | HIV infection, AIDS |
| RBC-CD4 | Sheffield Med. Tech (Houston TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| Valaciclovir | Glaxo Wellcome | genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-La Roche | HIV infection, AIDS, ARC, with AZT |
| Zidovudine; AZT | Glaxo Wellcome | HIV infection, AIDS, ARC, Kaposi's sarcoma, in combination with other therapies |

IMMUNO-MODULATORS

| Drug Name | Manufacturer | Indication |
|---|---|---|
| AS-101 | Wyeth-Ayerst | AIDS |
| Bropirimine | Pharmacia Upjohn | advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte | Amgen | AIDS, in combination |

-continued

| Drug Name | Manufacturer | Indication |
|---|---|---|
| Colony Stimulating Factor | | w/AZT |
| Remune | Immune Response Corp. | immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |

ANTI-INFECTIVES

| Drug Name | Manufacturer | Indication |
|---|---|---|
| Clindamycin with Primaquine | Pharmacia Upjohn | PCP |
| Fluconazole | Pfizer | cryptococcal meningitis, candidiasis |
| Pastille Nystatin Pastille | Squibb Corp. | prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | cryptosporidial diarrhea |
| Intraconazole-R51211 | Janssen Pharm. | histoplasmosis; cryptococcal meningitis |
| Trimetrexate | Warner-Lambert | PCP |

OTHER

| Drug Name | Manufacturer | Indication |
|---|---|---|
| Daunorubicin | NeXstar, Sequus | Karposi's sarcoma |
| Recombinant Human Erythropoietin | Ortho Pharm. Corp. | severe anemia assoc. with AZT therapy |
| Recombinant Human Growth Hormone | Serono | AIDS-related wasting, cachexia |
| Megestrol Acetate | Bristol-Myers Squibb | treatment of anorexia assoc. w/AIDS |
| Testosterone | Alza, Smith Kline | AIDS-related wasting |
| Total Enteral Nutrition | Norwich Eaton Pharmaceuticals | diarrhea and malabsorption related to AIDS |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Preferred combinations are simultaneous or alternating treatments of with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is indinavir, which is the sulfate salt of N-(2(R)-hydroxy-1(S)-indanyl)-2(R)-phenylmethyl-4-(S)-hydroxy-5-(1-(4-(3-pyridyl-methyl)-2 (S)-N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. The preparation of ddC, ddI and AZT are also described in EPO 0,484,071. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) zidovudine and lamivudine and 141W94 and 1592U89; (5) zidovudine and lamivudine.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl- pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of The present invention are employed. (For purposes of this application, topical application shall include mouth washes and gargles.)

The pharmaceutical composition and method of the present invention may further comprise other therapeutically active compounds as noted herein which are usually applied in the treatment of the above mentioned pathological conditions.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples.

Several methods for preparing the compounds of this invention are illustrated in the following Schemes and Examples.

According to one general process, (A), compounds of formula (I) may be prepared from a compound of formula (II)

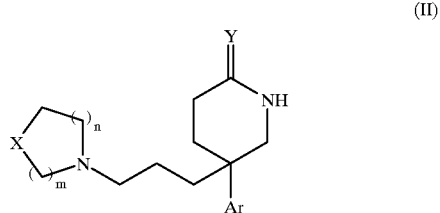

wherein Ar, X, Y, m and n are as defined in relation to formula (I), by reaction with a compound of the formula (III)

wherein R and Z are as defined in relation to formula (I) and LG represents a leaving group such as a halogen atom or an alkyl- or aryl-sulphonyloxy group, e.g. chlorine, bromine or iodine or a methylsulphonate or p-toluenesulphonate group, in the presence of a base.

For compounds wherein Y is two hydrogen atoms and Z is oxygen, suitable bases include organic bases such as tertiary amines, e.g. triethylamine, and inorganic bases such as alkali metal carbonates, e.g. sodium carbonate or potassium carbonate. Conveniently, the reaction is effected in a suitable organic solvent, such as dimethylformamide, acetonitrile or dichloromethane, conveniently at a temperature between room temperature and 100° C.

For compounds wherein Y is oxygen and Z is two hydrogen atoms, suitable bases include alkali metal hydrides, e.g. sodium hydride. Conveniently, the reaction is effected in a suitable organic solvent such as an ether, e.g. tetrahydrofuran, conveniently at a temperature between room temperature and 100° C.

According to another process, (B), compounds of formula (I) may be prepared from compounds of formula (IV):

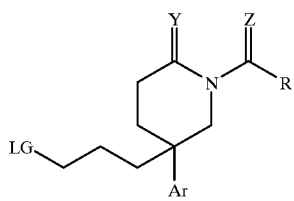

(IV)

wherein Ar, R Y and Z are as defined in relation to formula (I) and LG is as previously defined, by reaction with an amine of formula (V):

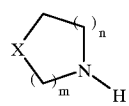

(V)

wherein X, m and n are as defined in relation to formula (I), in the presence of a base.

Suitable bases include organic bases such as tertiary amines, e.g. triethylamine, and inorganic bases such as alkali metal carbonates, e.g. sodium carbonate or potassium carbonate.

Conveniently, the reaction is effected in a suitable organic solvent, such as dimethylformamide, acetonitrile or dichloromethane, conveniently at a temperature between room temperature and 100° C.

Compounds of formula (II) may be prepared from compounds of formula (VI):

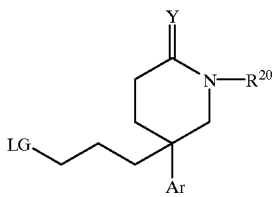

(VI)

wherein Ar and Y are as defined in relation to formula (I), LG is as previously defined, and $R^{20}$ is a suitable amine protecting group, such as an alkoxycarbonyl group, for example, tert-butoxycarbonyl, by reaction with an amine of formula (V) according to the method of process (B) above, followed by removal of any protecting group where present.

Compounds of formula (IV) may be prepared from compounds of formula (VII):

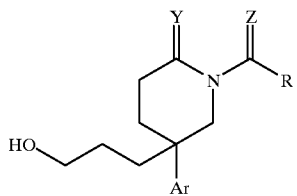

(VII)

by conventional methodology. For instance, where the desired leaving group is a halogen atom, by reaction with a corresponding halogen acid, such as hydrogen bromide or hydrogen iodide. Where the leaving group is an alkyl- or aryl-sulphonyloxy group, the compound of formula (VII) may be reacted with, for example, methanesulfonyl chloride or p-toluenesulfonyl chloride.

Alternatively, compounds of formula (IV) may be prepared by the reaction of a compound of formula (VIII):

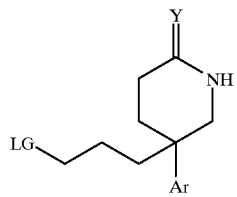

(VIII)

with a compound of formula (II) according to the method of process (A).

Compounds of formula (VII) may be prepared by the reaction of a compound of formula (IX):

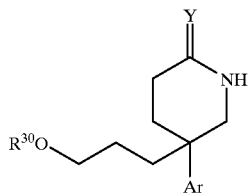

(IX)

where $R^{30}$ is a suitable hydroxy protecting group, for example, tetrahydropyran, with a compound of formula (II) according to the method of process (A), above, followed by removal of any protecting group where present.

Compounds of formula (IX) in which Y is two hydrogen atoms may be prepared by reduction of the corresponding compound of formula (IX) in which Y is an oxygen atom. Suitable reducing agents include hydrides such as lithium aluminium hydride in a suitable solvent, for example, tetrahydrofuran, conveniently at a temperature between room temperature and 100° C., for example, at about 60° C.

Alternatively, compounds of formula (IX) in which Y is two hydrogen atoms may be prepared in a two-step reaction from a compound of formula (X)

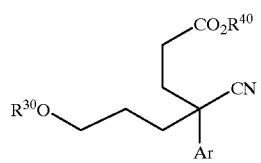

(X)

wherein $R^{30}$ is a suitable hydroxy protecting group as previously defined and $R^{40}$ is a $C_{1-6}$alkyl group, especially an ethyl group. Firstly the compound of formula (X) is reduced using, for example, lithium aluminium hydride as described above. The resulting compound of formula (Xa):

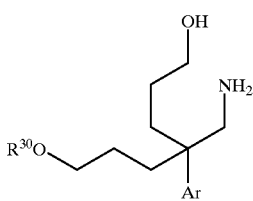

(Xa)

is then cyclized by converting the alcohol group to a leaving group using, for example, triphenyl phosphine, followed by the addition of diethyl azodicarboxylate (DEAD) in a suitable organic solvent, for example, dichloromethane, to complete the cyclization, this method being based upon that described by R. C. Bernotas and R. V. Cube in *Tetrahedron Letters* (1990) 91, 161–164.

Compounds of formula (IX) in which Y is an oxygen atom may also be prepared from a corresponding compound of formula (X), by hydrogenation in the presence of an excess of Raney™ nickel. A suitable solvent for this reaction is a mixture of ethanol and ammonia.

Compounds of formula (X) may be prepared from a compound of formula (XI):

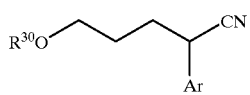

(XI)

by a Michael addition using a compound of the formula $H_2C=CHCO_2R^{40}$ and a suitable base, preferably, N-benzyltrimethyl-ammonium hydroxide (Triton B™).

Compounds of formula (XI) may be prepared by the alkylation of a compound of formula (XII) with a compound of formula (XIII):

(XII)

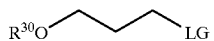

(XIII)

wherein Ar, $R^{30}$ and LG are as previously defined, using conventional conditions, for example, using a base such as sodium hydride in a suitable solvent such as tetrahydrofuran, preferably at a temperature between −25° C. and room temperature.

Compounds of formulae (III), (V), (XII) and (XIII) are commercially available, or may be prepared from commercially available starting materials using. conventional procedures well known to those skilled in the art.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

In particular, amino moieties may be protected by, for example, the formation of alkoxycarbonyl derivatives, e.g. tert-butoxycarbonyl and trichloroethoxycarbonyl, or benzyl, trityl or benzyloxycarbonyl derivatives. Subsequent removal of the protecting group is achieved by conventional procedures thus, for example, tert-butoxycarbonyl, benzyl or benzyloxycarbonyl groups may be removed by hydrogenolysis in the presence of a catalyst e.g. palladium; a trichloroethoxycarbonyl group may be removed with zinc dust; and a trityl group may be removed under acidic conditions using standard procedures.

Where hydroxyl groups require protection, this may be effected by the formation of esters or trialkylsilyl, tetrahydropyran or benzyl ethers. Such derivatives may be deprotected by standard procedures thus, for example, a tetrahydropyran ether derivative may be deprotected using hydrochloric acid in methanol.

In some cases the order of carrying out the foregoing reaction schemes may be varied to facilitate the reaction or to avoid unwanted reaction products.

The following examples are provided for the purpose of further illustration only and are not intended to be limitations on the disclosed invention.

INTERMEDIATE 1

3,4-Dichlorotetrahydropyranyloxypropyl-α-benzeneacetonitrile 3,4-Dichlorophenylacetonitrile (52.0 g, 0.280 mol) and 3-bromopropoxy-tetrahydropyrane (68.6 g, 1.1 eq) were mixed in tetrahydrofuran (350 ml) and cooled to −20° C. Sodium hydride (60% in oil, 30 g, 2.7 eq) was added during 25 minutes. The solution was allowed to warm to room temperature and stirred for 2 hours. The reaction was quenched carefully with water and partitioned with ethyl acetate and the aqueous phase was extracted with ethyl acetate (×2). The combined organic phase was washed with water (×2), brine (×1) and dried ($MgSO_4$). The solvent was evaporated and the residue was purified by flash chromatography using petroleum ether/dichloromethane (gradient 100:0 to 0:100) as eluant to provide the title compound as a viscous yellow oil (77.0 g, 84% yield). $^1$H NMR (250 MHz, $CDCl_3$): δ 7.48 (2H, m) 7.20 (1H, dd, $J_1$=8.29 Hz, $J_2$=2.17 Hz) 4.55 (1H, t, J=1.74 Hz) 3.92-3.74 (2H, m) 3.55-3.39 (2H, m) 2.07-1.97 (2H, m) 1.83-1.71 (4H, m) 1.55 (4H, m) 1.26 (1H, t, J=14.29 Hz). m/z (ES+) 327/329 due to chlorine isotope pattern.

INTERMEDIATE 2

4-[3-Tetrahydropyranyloxypropyl]-4-cyano-4-[3,4-dichlorophenyl]-ethylbutanoate

The nitrile (Intermediate 1) (30.15 g, 0.0919 mol) was dissolved in 1,4-dioxane (200 ml). Ethyl acrylate (17.56 g, 1.7 eq) and Triton B™ (5 ml, 40 wt %, methanol) were added and the solution was stirred at 80° C. for 29 hours at room temperature. The reaction was quenched with ammonium chloride and extracted with diethyl ether (×2). The combined organic phase was washed with water (×2), brine (×1) and dried ($MgSO_4$). The solvent and unreacted ethyl acrylate were evaporated to provide the title compound as a viscous yellow oil (37.4 g, 95% yield). $^1$H NMR (250 MHz, $CDCl_3$): δ 7.48 (2H, m) 7.26 (1H, dd, $J_1$=8.29 Hz, $J_2$=2.17 Hz) 4.51 (1H, dt, $J_1$=10.23 Hz, $J_2$=3.21 Hz) 4.17-4.03 (2H, m) 3.86-3.65 (2H, m) 3.51-3.32 (2H, m) 2.54-1.96 (6H, m) 1.77-1.66 (4H, m) 1.51 (4H, m) 1.24 (3H, m). m/z (ES+) 428/430 due to chlorine isotope pattern

INTERMEDIATE 3

5-[3-Tetrahydropyranyloxypropyl]-5-[3,4-dichlorophenyl]-piperidin-2-one

The ester nitrile (Intermediate 2) (26.66 g, 0.062 mol) was dissolved in ethanol (140 ml) and ammonia (22 ml).

Raney™ nickel catalyst was added (8 "scoops") and the solution was hydrogenated at 40 psi for 48 hours (the hydrogen was recharged several times the first couple of hours). The solution was filtered, keeping the catalyst wet at all times, the solvent was evaporated under high vacuum and the residue was purified by flash chromatography using ethyl acetatelmethanol (gradient 100:0 to 80:20) as eluant to provide the title compound as a clear yellow viscous oil (18.3 g, 76% yield). $^1$H NMR (360 MHz, CDCl$_3$): δ 7.41 (2H, m) 7.15 (1H, dd, J$_1$=8.45 Hz, J$_2$=2.31 Hz) 7.10 (1H, s) 4.45 (1H, dt, J$_1$=10.23 Hz, J$_2$=3.21 Hz) 3.77 (1H, m) 3.69-3.56 (2H, m) 3.45 (1H, m) 3.36 (1H, dd, J$_1$=12.71 Hz, J$_2$=undetectable) 3.25 (1H, m) 2.16-2.04 (2H, m) 1.88-1.79 (2H, m) 1.65 (2H, m) 1.51 (4H, m) 1.33-1.18 (3H, m).

INTERMEDIATE 4

5-[3-Tetrahydropyranyloxypropyl]-5-[3,4-dichlorophenyl]-1-benzylpiperidin-2-one

The piperidinone (Intermediate 3) (4.43 g, 0.010 mol) was dissolved in tetrahydrofuran (40 ml). Sodium hydride (60% in oil, 0.44 g, 1.1 eq) and benzyl bromide (1.88 g, 1.1 eq) were added and the mixture stirred at room temperature for 16 hours. The reaction was quenched with water and extracted with ethyl acetate (×3). The combined organic phase was washed with water (×1), brine (×1) and dried (MgSO$_4$). The solvent was evaporated and the residue was purified by flash chromatography using ethyl acetate/petroleum ether (50:50) as eluant to provide the title compound. $^1$H NMR (250 MHz, CDCl$_3$) (this spectrum only contains very broad peaks so in the following only the chemical shifts and the integrations are given) δ 7.34 (6H) 7.08 (1H) 6.80 (1H) 4.86 (1H) 4.42 (1H) 3.75 (1H) 3.52 (3H) 3.22 (2H) 2.44 (1H) 2.12 (2H) 1.67 (4H) 1.51 (4H) 1.17 (3H).

INTERMEDIATE 5

5-[3-Hydroxypropyl]-5-[3,4-dichlorophenyl]-1-benzylpiperidin-2-one

The THP protected piperidinone (Intermediate 4) (4.11 g, 8.65 mmol) was deprotected by stirring with 3M hydrochloric acid/methanol (50 ml) for 2 hours. The solvent was evaporated and the residue was redissolved in ethyl acetate and washed with sodium bicarbonate (×1), brine (×1) and dried (MgSO$_4$). The solvent was evaporated to afford the title compound as a yellow oil which was used without further purification.

INTERMEDIATE 6

5-[3-Methanesulfonyloxypropyl]-5-[3,4-dichlorophenyl]-1-benzylpiperidin-2-one

The deprotected piperidinone (Intermediate 5) (3.28 g, 8.39 mmol) was dissolved in dichloromethane (25 ml) on a water bath. Triethylamine (1.27 g, 1.5 eq) was added followed by methanesulfonyl chloride (1.05 g, 1.1 eq). The mixture was stirred for 1.5 hours at room temperature and then quenched with sodium bicarbonate. The aqueous phase was extracted with dichloromethane (×2) and the combined organic phase was washed with water (×1), brine (×1) and dried (MgSO$_4$). The solvent was evaporated and the residue was purified by flash chromatography using ethyl acetate/petroleum ether (gradient 50:50 to 100:0) as eluant to provide the title compound as a clear gum. $^1$H NMR (250 MHz, CDCl$_3$): δ 7.38-7.26 (6H, m) 7.08 (1H, d, J=2.28 Hz) 6.78 (1H, dd, J$_1$=8.44 Hz, J$_2$=2.28 Hz) 4.87 (1H, d, J=14.31 Hz) 4.36 (1H, d, J=14.31 Hz) 4.02 (1H, t, J=6.15 Hz) 3.54 (1H, d, J=12.02 Hz) 3.27 (1H, d, J=12.02 Hz) 2.94 (3H, s) 2.51-2.41 (1H, m) 2.26-1.97 (3H, m) 1.84-1.57 (2H, m) 1.36-1.24 (2H, m).

INTERMEDIATE 7

5-(3-Tetrapyranyloxypropyl)-5-[3,4-dichlorophenl]-piperidine

The THP protected piperidinone (Intermediate 3) (13.74 g, 0.036 mol) was dissolved in tetrahydrofuran (100 ml) and 1M lithium aluminium hydride (78 ml, 2 eq) was added. The solution was stirred at 60° C. on an oil bath for 2 hours. The reaction was quenched carefully with 2M sodium hydroxide (15 ml) and water (15 ml). The aqueous phase was extracted with ethyl acetate (×2) and the combined organic phase was washed with water (×1), brine (×1) and dried (MgSO$_4$). The solvent was evaporated to provide the title compound (10.0 g, 76% yield). $^1$H NMR (250 MHz, CDCl$_3$): δ 7.41-7.38 (2H, m) 7.17 (1H, dd, J$_1$=8.47 Hz, J$_2$=2.23 Hz) 4.46 (1H, t, J=3.51 Hz) 3.84-3.75 (1H, m) 3.69-3.56 (1H, m) 3.49-3.41 (1H, m) 3.28-3.19 (2H, m) 2.86-2.71 (2H, m) 2.12-2.05 (1H, m) 1.85-1.37 (12H, m) 1.31-1.14 (3H, m).

INTERMEDIATE 8

5-(3-Tetrapyranyloxypropyl)-5-[3,4-dichlorophenyl]-piperidine (Alternative route)

Step A) 4-(3-Tetrahydropyranyloxypropyl)-4-cyano-4-[3,4-dichlorophenyl]-butan-1-ol The nitrile ester (Intermediate 2) (2.07 g, 4.84 mmol) was dissolved in tetrahydrofuran (10 ml) and cooled on a ice-bath. lithium aluminium hydride (1M, THF, 14.5 ml, 3 eq) was added over 10 minutes. The solution was then stirred at 60° C. on an oil bath for 2 hours after which it quenched carefully with sodium hydroxide (2M, 2 ml) and water (2 ml). The solution was filtered through a Hyflo™ filter and the filtrate was dried (MgSO$_4$) and evaporated to provide the title compound (1.71 g, 91% yield).

Step B) 5-(3-Tetrapyranyloxypropyl)-5-[3,4-dichlorophenyl]-piperidine

The amino alcohol of Step (A) (1.70 g, 436 mmol) was dissolved in anhydrous dichloromethane and triphenyl phosphine (1.26 g, 1.1 eq) was added. After stirring for 5 minutes diethyl azodicarboxylate (0.73 g, 1 eq) was added and the mixture was stirred for 5 hours. The solution was diluted with water and extracted with dichloromethane (×2). The combined organic phase was washed with water (×2), brine (×1), dried (MgSO$_4$) and the solvent was evaporated. The residue was purified by flash chromatography using ethyl acetate/methanol/ammonia (gradient 100:0:0 to 90:10:0.2) as eluant to provide the title compound (1.123 g, 69% yield).

INTERMEDIATE 9

5-(3-Tetrapyranyloxypropyl)-5-[3,4-dichlorophenyl]-1-benzoylpiperidine

The THP protected piperidine (Intermediate 7) (10.0 g, 0.027 mol) was dissolved in dichloromethane (50 ml) on an ice-bath. Triethylamine (3.00 g, 1.1 eq) was added. Benzoyl chloride (4.18 g, 1.1 eq) was dissolved in dichloromethane (50 ml) and added dropwise. The reaction was allowed to warm to 23° C., stirred for 2 hours and then quenched with sodium bicarbonate and extracted with dichloromethane (×3). The combined organic phase was washed with water (×1), brine (×1) and dried (MgSO$_4$). The solvent was removed in vacuo to provide the title compound as a brown solid. This material was used without further purification. $^1$H NMR at 353K (360 MHz, DMSO): δ 7.53 (1H, d, J=8.58 Hz) 7.50 (1H, m) 7.40 (3H, m) 7.31 (1H, m) 7.23 (2H, m) 4.41 (1H, m) 4.12 (1H, m) 3.66 (1H, m) 3.51-3.36 (5H, m) 3.22 (1H, m) 2.10 (1H, m) 1.84 (1H, m) 1.68 (2H, m) 1.56 (2H, m) 1.42 (6H, m) 1.18 (2H, m).

INTERMEDIATE 10
5-(3-Hydroxypropyl)-5-[3,4-dichlorophenyl]-1-benzoylpiperidine The THP protected amide (Intermediate 9) (12.8 g, 0.027 mol) was deprotected by stirring with 3M hydrochloric acid in methanol (150 ml) for 2 hours. The solvent was removed in vacuo and the residue was redissolved in ethyl acetate and washed with sodium bicarbonate (×1), water (×1) and (MgSO$_4$). The solvent was evaporated to provide the title compound. This material was used without further purification. $^1$H NMR at 353K (360 MHz, DMSO): δ 7.53 (1H, d, J=8.47 Hz) 7.49 (1H, s) 7.41 (3H, m) 7.30 (1H, m) 7.22 (2H, m) 4.18 (1H, m) 4.04 (1H, m) 3.43-3.22 (5H, m) 2.11 (1H, m) 1.81 (1H, m) 1.69-1.54 (3H, m) 1.36 (1H, m) 1.04 (2H, m).

INTERMEDIATE 11
5-(3-Methanesulfonylpropyl)-5-[3,4-dichlorophenyl]-1-benzoylpiperidine The amido alcohol (Intermediate 10) (11.3 g, 0.029 mol) was dissolved in dichloromethane (100 ml), triethylamine (4.36 g, 1.5 eq) and then methanesulfonyl chloride (3.63 g, 1.1 eq) were added and the mixture stirred for 1 hour. The reaction was quenched with sodium bicarbonate and extracted with dichloromethane (×3). The organic layer was washed with water (×1), brine (×1) and dried (MgSO$_4$). The solvent was evaporated and the residue was purified by flash chromatography using ethyl acetate/petroleum ether (50:50 and 100:0) as eluant to provide the title compound as a gum (8.82 g, 63% yield). m/z (ES+) 470.

EXAMPLE 1
5-[3-{4,4-(N-Sulfonamidomethyl-3,3-indolyl)piperidino}propyl]-5-[3,4-diphenyl]-1-benzylpiperidin-2-one The lactam mesylate (Intermediate 6) (0.433 g, 0.923 mmol) was dissolved in dimethylformamide (3 ml). Potassium carbonate (0.262 g, 2 eq) and 4,4-[N-sulfonamidomethyl-3,3-indolyl]-piperidine (0.268 g, 1.1 eq) was added and stirred at 60° C. on an oil bath for 16 hours. The solution was diluted with water (×15) and extracted with ethyl acetate (×2). The combined organic phase was washed with water (×2), brine (×1) and dried (MgSO$_4$). The solvent was evaporated and the residue was purified by flash chromatography using dichloromethane/methanol (gradient 100:0 to 95:5) as eluant to provide the title compound as a white amorphous solid (219 mg, 37% yield). $^1$H NMR (250 MHz, CDCl$_3$): δ 7.42-7.02 (11H, m) 6.80 (1H, dd, J$_1$=8.45 Hz, J$_2$=2.30 Hz) 4.86 (1H, d, J=14.33 Hz) 4.39 (1H, d, J=14.33 Hz) 3.74 (2H, s) 3.56 (1H, d, J=12.76 Hz) 3.26 (1H, d, J=12.76 Hz) 2.88 (3H, s) 2.71 (2H, br.s) 2.50-2.41 (1H, m) 2.25-1.46 (13H, m) 1.08 (2H, m). m/z (ES+) 640.

EXAMPLE 2
5-[3-{4-(2-Keto-1-benzimidazolinyl)-piperidino}propyl]-5-[3,4-dichlorophenyl]-1-benzylpiperidin-2-one The lactam mesylate (Intermediate 6) (0.336 g, 0.716 mmol) was dissolved in dimethylformamide (5 ml). Potassium carbonate (0.198 g, 2 eq) and 4-[2-keto-1-benzimidazolinyl]-piperidine (0.175 g, 1.1 eq) was added and stirred at 60° C. on an oil bath for 16 hours. The solution was diluted with water (×15) and extracted with ethyl acetate (×2). The combined organic phase was washed with water (×2), brine (×1) and dried (MgSO$_4$). The solvent was evaporated and the residue was purified by flash chromatography (three times) using dichloromethane/methanol (gradient 100:0 to 96:4) as eluant to provide the title compound as a white amorphous solid (13 mg, 3% yield). $^1$H NMR (250 MHz, CDCl$_3$): δ 7.42-7.20 (7H, m) 7.12-7.00 (4H, m) 6.81 (1H, dd, J$_1$=8.45 Hz, J$_2$=2.30 Hz) 4.86 (1H, d, J=14.33 Hz) 4.40 (1H, d, J=14.33 Hz) 4.30 (1H, m) 3.56 (1H, d, J=12.76 Hz) 3.26 (1H, d, J=12.76 Hz) 2.86 (2H, br.s) 2.52-2.01 (10H, m) 1.78-1.68 (4H, m) 1.60-1.47 (1H, m) 1.09 (2H, m). m/z (ES+) 591

EXAMPLE 3
5-[3-{4-Acetyl-4-phenyl-piperidino}propyl]-5-[3,4-dichlorophenyl]-1-benzylpiperidin-2-one The lactam mesylate, (Intermediate 6) (0.437 g, 0.932 mmol) was dissolved in dimethylformamide (5 ml). Potassium carbonate (0.385 g, 3 eq) and 4-acetyl-4-phenylpiperidine hydrochloride (0.248 g, 1.1 eq) was added and stirred at 60° C. on an oil bath for 16 hours. The solution was diluted with water (×15) and extracted with ethyl acetate (×2). The combined organic phase was washed with water (×2), brine (×1) and dried (MgSO$_4$). The solvent was evaporated and the residue was purified by flash chromatography using dichloromethane/methanol (gradient 99:1 to 97:3) as eluant to provide the title compound as a white amorphous solid (220 mg, 41% yield). $^1$H NMR (250 MHz, CDCl$_3$): δ 7.37-7.24 (11H, m) 7.08 (1H, d, J=2.18 Hz) 6.78 (1H, dd, J$_1$=8.45 Hz, J$_2$=2.18 Hz) 4.86 (1H, d, J=14.31 Hz) 4.36 (1H, d, J=14.31 Hz) 3.53 (1H, d, J=12.70 Hz) 3.23 (1H, d, J=12.70 Hz) 2.49-2.38 (6H, m) 2.22-1.87 (11H, m) 1.69 (1H, td, J$_1$=12.78 Hz, J$_2$=5.51 Hz) 1.48 (1H, td, J$_1$=12.78 Hz, J$_2$=5.51 Hz) 1.03 (2H, m). m/z (ES+) 577

EXAMPLE 4
5-[3-{1-Phenyl-1,3,8-triazaspiro[4.5]decan-4-one}propyl]-5-[3,4-dichlorophenyl]-1-benzylpiperidin-2-one The lactam mesylate (Intermediate 6) (0.420 g, 0.896 mmol) was dissolved in dimethylformamide (6 ml). Potassium carbonate (0.493 g, 4 eq) and 1-phenyl-1,3,8-triazaspiro[4.5]decan-4-one (0.231 g, 1.1 eq) was added and stirred at 60° C. on an oil bath for 16 hours. The solution was diluted with water (×15) and extracted with ethyl acetate (×2). The combined organic phase was washed with water (×2), brine (×1) and dried (MgSO$_4$). The solvent was evaporated and the residue was purified by flash chromatography using dichloromethane/methanol (gradient 99:1 to 95:5) as eluant to provide the title compound as a white amorphous solid (186 mg, 34% yield). 1H NMR (360 MHz, CDCl$_3$): δ 7.39-7.23 (9H, m) 7.10 (1H, d, J=2.25Hz) 6.87 (3H, m) 6.81 (1H, dd, J$_1$=8.45 Hz, J$_2$=2.25 Hz) 4.85 (1H, d, J=14.34 Hz) 4.69 (2H, s) 4.39 (1H, d, J=14.34 Hz) 3.55 (1H, d, J=12.70 Hz) 3.26 (1H, d, J=12.70 Hz) 2.65-2.42 (6H, m) 2.23-2.12 (4H, m) 2.06-1.97 (2H, m) 1.74 (1H, td, J$_1$=12.67 Hz, J$_2$=5.02 Hz) 1.66 (2H, d, J=13.15 Hz) 1.52 (1H, td, J$_1$=12.67 Hz, J$_2$=5.02 Hz) 1.06 (2H, m). m/z (ES+) 605

EXAMPLE 5
5-[3-{4,4-(N-Sulfonamidomethyl-3,3-indolyl)piperidino}propyl]-5-[3,4-diphenyl]-1-benzoylpiperidine The amide mesylate (Intermediate 11) (0.70 g, 1.49 mmol) was dissolved in dimethylformamide (8 ml). Potassium carbonate (0.44 g, 2 eq) and 4,4-(N-sulfonamido-3,3-indolyl)-piperidine (0.48 g, 1.2 eq) were added and the mixture was stirred on an oil bath at 60° C. for 16 hours. The reaction was diluted with water (×15) and extracted with ethyl acetate (×2). The organic phase was washed with water (×1), brine (×1) and dried (MgSO$_4$). The solvent was evaporated and the residue was purified twice by flash chromatography using dichloromethane/methanol (gradient 99:1 and 98:2) as eluant to provide the title compound as a white amorphous solid (178 mg, 19% yield). $^1$H NMR at 353K (360 MHz, DMSO): δ 7.54 (1H, d, J=8.47 Hz) 7.52 (1H, s)

7.42 (3H, m) 7.33 (1H, m) 7.21 (5H, m) 7.02 (1H, t, J=7.34 Hz) 4.11 (1H, br.s) 3.73 (2H, s) 3.53 (1H, d, J=13.32 Hz) 3.36 (2H, br.s) 2.98 (3H, s) 2.62 (2H, m) 2.17 (3H, m) 1.95-1.75 (5H, m) 1.64-1.54 (5H, m) 1.39 (1H, br.s) 1.07 (2H, m). m/z (ES+) 640

EXAMPLE 6
5-[3-{4-(2-Keto-1-benzimidazolinyl)-piperidino}propyl]-5-[3,4-dichlorophenyl]-1-benzoylpiperidine The amide mesylate (Intermediate 11) (0.660 g, 1.41 mmol) was dissolved in dimethylformamide (5 ml). Potassium carbonate (0.388 g, 2 eq) and 4-(2-keto-1-benzimidazolinyl)-piperidine (0.366 g, 1.2 eq) were added and the mixture was stirred on an oil bath at 60° C. for 16 hours. The reaction was diluted with water (×15) and extracted with ethyl acetate (×2). The organic phase was washed with water (×1), brine (×1) and dried (MgSO$_4$). The solvent was evaporated and the residue was purified by flash chromatography using dichloromethane/ methanol (gradient 100:0 to 94:6) as eluant to provide the title compound as a white amorphous solid (174 mg, 21% yield). $^1$H NMR at 353K (360 MHz, DMSO): δ 10.52 (1H, s) 7.54 (1H, d, J=8.47 Hz) 7.52 (1H, s) 7.42 (3H, m) 7.34 (1H, m) 7.24 (2H, m) 7.13 (1H, m) 6.94 (3H, m) 4.06 (2H, m) 3.53 (1H, d, J=13.46 Hz) 3.37 (2H, br.s) 2.78 (2H, m) 2.29 (2H, m) 2.17 (3H, m) 1.97-1.87 (3H, m) 1.60 (5H, m) 1.38 (1H, br.s) 1.08 (2H, m). m/z (ES+) 591

EXAMPLE 7
5-[3-{4-Acetyl-4-phenyl-piperidino}propyl]-5-[3,4-dichlorophenyl]-1-benzoylpiperidine The amide mesylate (Intermediate 11) (0.567 g, 1.21 mmol) was dissolved in dimethylformamide (8 ml). Potassium carbonate (0.333 g, 2 eq) and 4-acetyl-4-phenylpiperidine (0.270 g, 1.1 eq) were added and the mixture was stirred on an oil bath at 60° C. for 16 hours. The reaction was diluted with water (×15) and extracted with ethyl acetate (×2). The organic phase was washed with water (×1), brine (×1) and dried (MgSO$_4$). The solvent was evaporated and the residue was purified by flash chromatography. using dichloromethane/methanol (gradient 100:0 to 98:2) as eluant to provide the title compound as a white amorphous solid (123 mg, 18% yield). $^1$H NMR at 353K (360 MHz, DMSO): δ 7.54 (1H, d, J=8.47 Hz) 7.52 (1H, s) 7.42-7.23 (1H, m) 4.08 (1H, m) 3.52 (1H, d, J=13.37 Hz) 3.36 (2H, br.s) 2.37-2.30 (4H, m) 2.06 (5H, m) 1.95-1.85 (6H, m) 1.57 (3H, m) 1.37 (1H, br.s) 1.03 (2H, m). m/z (ES+) 577

EXAMPLE 8
5-[3-{1-Phenyl-1,3,8-triazaspiro[4.5]decan-4-one}propyl]-5-[3,4-dichlorophenl]-1-benzoylpiperidine The amide mesylate (Intermediate 11) (0.760 g, 1.62 mmol) was dissolved in dimethylformamide (8 ml). Potassium carbonate (0.847 g, 3.8 eq) and 1-phenyl-1,3,8-triazaspiro[4.5]decan-4-one (0.270 g, 1.1 eq) were added and the mixture was stirred on an oil bath at 60° C. for 16 hours. The reaction was diluted with water (×15) and extracted with ethyl acetate (×2). The organic phase was washed with water (×1), brine (×1) and dried (MgSO$_4$). The solvent was evaporated and the residue was purified by flash chromatography using dichloromethane/ methanol (gradient 100:0 to 98:2) as eluant to provide the title compound as a offwhite amorphous solid (333 mg, 34% yield). $^1$H NMR at 353K (360 MHz, DMSO): δ 8.29 (1H, s) 7.52 (2H, d, J=8.47 Hz) 7.41 (3H, m) 7.33 (1H, br.s) 7.23 (4H, m) 6.88 (2H, d, J=8.11 Hz) 6.78 (1H, t, J=7.28 Hz) 4.56 (2H, s) 4.15 (1H, m) 3.52 (1H, d, J=13.40 Hz) 3.38 (2H, br.s) 2.61-2.38 (6H, m) 2.19 (3H, m) 1.87 (1H, m) 1.72-1.51 (5H, m) 1.39 (1H, br.s) 1.10 (2H, m). m/z (ES+) 605

EXAMPLE 9
5-[3-{4,4-(1,1-Indanyl)piperidino}propyl]-5-[3,4-diphenyl]-1-benzoylpiperidine By employing essentially the procedures described above, the title compound was prepared from the amide mesylate (Intermediate 11) and 4,4-(1,1-indanyl)-piperidine. $^1$H NMR (DMSO-d$_6$): δ 7.54 (2H, m) 7.40 (3H, m) 7.32 (1H, br.m) 7.24 (2H, m) 7.10 (4H, m) 4.06 (1H, br.m) 3.53 (1H, d, J=13.4 Hz) 3.36 (2H, br.s) 2.81 (2H, t, J=7.2 Hz) 2.49 (2H, m) 2.18-1.60 (14H, m) 1.37 (4H, m). m/z 561 (MH+, 100%).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A method for antagonism of the activity of the chemokine receptor CCR-5 selectively with respect to the activity of non-chemokine receptors in a mammal in need thereof comprising the administration of an effective amount of a compound of formula I:

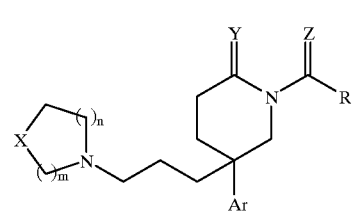

(I)

wherein m is zero, 1 or 2;

n is 1, 2 or 3, with the proviso that the sum of m+n is 3;

X is:

one of Y and Z is =O whereas the other represents two hydrogen atoms;

Ar is selected from the group consisting of:
unsubstituted phenyl;
phenyl which is substituted by 1, 2 or 3 substituents selected from:
hydroxy, cyano, halogen, trifluoromethyl, C$_{1-6}$alkyl, C$_{2-6}$alkenyl, C$_{2-6}$alkynyl, C$_{3-7}$cycloalkyl, C$_{3-7}$cycloalkylC$_{1-4}$alkyl, and C$_{1-6}$alkoxy;

thienyl; benzothienyl; napthyl; unsubstituted indolyl; and indolyl which is substituted on the nitrogen atom by a $C_{1-4}$alkyl group;

R is selected from the group consisting of:
unsubstituted phenyl; and
phenyl substituted by 1, 2 or 3 substituents selected from: hydroxy, cyano, halogen, trifluoromethyl, $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, and $C_{1-6}$alkoxy;

$R^1$ is selected from the group consisting of:
hydrogen; $C_{1-6}$alkyl;
$C_{1-6}$alkyl substituted by 1 or 2 substituents selected from: hydroxy, —$OR^3$, oxo, —$NHCOR^3$, —$NR^3R^4$, cyano, halogen, trifluoromethyl, unsubstituted phenyl, and phenyl substituted by 1 or 2 substituents selected from: hydroxy, cyano, halogen and trifluoromethyl;
unsubstituted phenyl;
phenyl substituted by 1, 2 or 3 substituents selected from: hydroxy, cyano, —$C(O)NR^3R^4$, —$NR^3R^4$, —$NR^3COR^4$, halogen, trifluoromethyl, $C_{1-4}$alkyl, —$S(O)_pC_{1-4}$alkyl and —$C(O)R^3$; unsubstituted aryl;
aryl substituted by 1, 2 or 3 substituents selected from: hydroxy, cyano, —$C(O)NR^3R^4$, —$NR^3R^4$, —$NR^3COR^4$, halogen, trifluoromethyl, $C_{1-4}$alkyl, $S(O)_pC_{1-4}$alkyl and —$C(O)R^3$; and
a saturated heterocyclic ring of 4, 5 or 6 ring atoms which ring contains 1 or 2 nitrogen atoms, one of which may be at the point of attachment to the remainder of the molecule, and optionally containing in the ring an oxygen atom, which ring is substituted on any available nitrogen atom by a group $R^5$ and which ring may be further substituted by a group selected from: hydroxy$C_{1-4}$alkyl, $C_{1-4}$alkoxy$C_{1-4}$alkoxy, oxo and $COR^3$, and which ring may have fused thereto a phenyl ring, wherein the phenyl ring may be substituted by 1 or 2 substituents selected from: hydroxy, cyano, —$C(O)NR^3R^4$, —$NR^3R^4$, —$NR^3COR^4$, halogen, trifluoromethyl, $C_{1-4}$alkyl, —$S(O)_pC_{1-4}$alkyl, and —$C(O)R^3$;

$R^2$ is selected from:
$C_{1-6}$alkyl hydroxy$C_{1-6}$alkyl, hydroxy, $OR^3$, halogen, trifluoromethyl, nitro, cyano, —$NR^3R^4$, —$NHCOR^3$, —$NR^3COR^4$, —$NHCO_2R^3$, —$NR^3CO_2R^4$, —$NHS(O)_pR^3$, —$NR^3S(O)_pR^4$, —$CONR^3R^4$, —$COR^3$, —$CO_2R^3$ and —$S(O)_pR^3$;
or $R^1$ and $R^2$ are joined together to form a 5- or 6-membered non-aromatic ring which may contain in the ring 1 or 2 groups of the formula —$NR^5$—, which ring is optionally substituted by an oxo group and which ring may be substituted by, or have fused thereto, a phenyl group, wherein the phenyl ring may be substituted by 1 or 2 substituents selected from: hydroxy, cyano, —$C(O)NR^3R^4$, —$NR^3R^4$, —$NR^3COR^4$, halogen, trifluoromethyl, $C_{1-4}$alkyl, -$S(O)_pC_{1-4}$alkyl, and —$C(O)R^3$;

$R^3$ and $R^4$ are each independently selected from:
hydrogen;
unsubstituted $C_{1-6}$alkyl;
$C_{1-6}$alkyl substituted by 1 or 2 substituents selected from unsubstituted: phenyl, hydroxy, oxo, cyano, $C_{1-4}$alkoxy and trifluoromethyl;
$C_{1-6}$alkoxy;
unsubstituted phenyl; and
phenyl substituted by 1, 2 or 3 substituents selected from: hydroxy, $C_{1-4}$alkyl, cyano, halogen, and trifluoromethyl;

or the group —$NR^3R^4$ is a saturated or partially saturated heterocyclic ring of 4 to 7 ring atoms, which ring may optionally contain in the ring one oxygen or sulfur atom or a group selected from: —NR, —S(O)— or —$S(O)_2$— and which ring may be optionally substituted by one or two groups selected from: hydroxy$C_{1-4}$alkyl, $C_{1-4}$alkoxy$C_{1-4}$alkyl, oxo, —$COR^6$ and —$CO_2R^6$;

$R^5$ is selected from:
hydrogen, $C_{1-4}$alkyl, —$S(O)_2C_{1-4}$alkyl, —$C(O)R^3$, unsubstituted phenyl and benzyl;

$R^6$ is selected from: hydrogen or $C_{1-4}$alkyl; and p is zero, 1 or 2;

or a pharmaceutically acceptable salt thereof.

2. The method of claim 1 wherein the compound of Formula I:

Ar is unsubstituted phenyl or phenyl substituted by 1, 2 or 3 substituents selected from: hydroxy, cyano, halogen, triflouromethyl, $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, and $C_{1-6}$alkoxy; or a pharmaceutically acceptable salt thereof.

3. The method of claim 1 wherein the compound of Formula I:

R is unsubstituted phenyl or phenyl substituted by 1, 2 or 3 substituents selected from: hydroxy, cyano, halogen, trifluoromethyl, $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, and $C_{1-6}$alkoxy;

or a pharmaceutically acceptable salt thereof.

4. The method of claim 1 wherein the compound of Formula I:

X is

wherein:
$R^1$ is unsubstituted phenyl, or a saturated heterocyclic ring of 5 ring atoms which ring contains 1 or 2 nitrogen atoms, one of which is at the point of attachment to the remainder of the molecule, which ring is substituted on any available nitrogen atom by a group $R^5$, where $R^5$ is hydrogen, and which ring is substituted by an oxo group, and which ring has fused thereto a phenyl ring, wherein the phenyl ring is unsubstituted or substituted by 1 or 2 substituents selected from: hydroxy, cyano, —$C(O)NR^3R^4$, —$NR^3R^4$, —$NR^3COR^4$, halogen, trifluoromethyl, $C_{1-4}$alkyl, —$S(O)_pC_{1-4}$alkyl, and —$C(O)R^3$;

$R^2$ is hydrogen or —$COR^3$, where $R^3$ is $C_{1-3}$alkyl;

or R and R are joined together to form a 5-membered nonaromatic ring which optionallly contains in the ring 1 or 2 groups of the formula $NR^5$, which ring is optionally substituted by an oxo group and which ring may be substituted by, or have fused thereto, a phenyl group, wherein the phenyl ring is unsubstituted or substituted by 1 or 2 substituents selected from: hydroxy, cyano, —$C(O)NR^3R^4$, —$NR^3R^4$, —$NR^3COR^4$, halogen, trifluoromethyl, $C_{1-4}$alkyl, —$S(O)_pC_{1-4}$alkyl, and —$C(O)R^3$;

or a pharmaceutically acceptable salt thereof.

5. The method of claim 1 wherein the compound of Formula I: m is 2 and n is 1;

or a pharmaceutically acceptable salt thereof.

6. The method of claim 1 wherein the compound is of the formula (Ia):

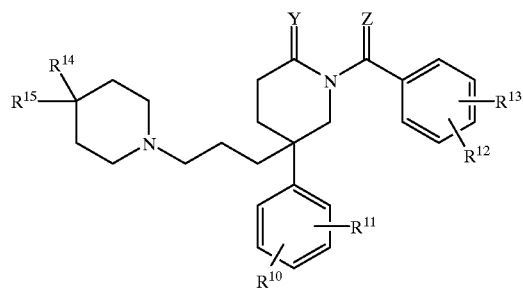

(Ia)

wherein:

R$^{10}$, R$^{11}$, R$^{12}$ and R$^{13}$ are selected from: hydrogen and halogen;

R$^{14}$ is an unsubstituted phenyl group or a saturated heterocyclic ring of 5 ring atoms which ring contains 1 or 2 nitrogen atoms, one of which is at the point of attachment to the remainder of the molecule, which ring is substituted on any available nitrogen atom by a group R$^5$, and which ring may be substituted by an oxo group, and which ring has fused thereto a phenyl ring, wherein the phenyl ring may be substituted by 1 or 2 substituents selected from: hydroxy, cyano, —C(O)NR$^3$R$^4$, —NR$^3$R$^4$, —NR$^3$COR$^4$, halogen, trifluoromethyl, C$_{1-4}$alkyl, —S(O)$_p$C$_{1-4}$alkyl, and —C(O)R$^3$;

R$^{15}$ is —COR$^3$, where R$^3$ is C$_{1-6}$alkyl;

or R$^{14}$ and R$^{15}$ are joined together to form a 5-membered non-aromatic ring which may contain in the ring 1 or 2 groups of the formula NR$^5$, which ring is optionally substituted by an oxo group and which ring may be substituted by, or have fused thereto, a phenyl group, wherein the phenyl ring may be substituted by 1 or 2 substituents selected from: hydroxy, cyano, —C(O)NR$^3$R$^4$, NR$^3$R$^4$, —NR$^3$R$^4$, halogen, trifluoromethyl, C$_{1-4}$alkyl, —S(O)$_p$C$_{1-4}$alkyl, and —C(O)R$^3$; and one of Y and Z is =O whereas the other represents two hydrogen atoms;

or a pharmaceutically acceptable salt thereof.

7. The method of claim 6 wherein the compound of formula (Ia):

R$^{10}$ and R$^{11}$ each are chlorine;

R$^{12}$ and R$^{13}$ each are hydrogen;

R$^{14}$ is unsubstituted phenyl;

R$^{15}$ is —COCH$_3$;

or R$^{14}$ and R$^{15}$ are joined together to form a 5-membered non-aromatic ring which may contain in the ring 1 or 2 groups of the formula —NR$^5$—, which ring is optionally substituted by an oxo group and which ring may be substituted by, or have fused thereto, an unsubstituted phenyl group, wherein R$^5$ is selected from: hydrogen, —S(O)$_2$CH$_3$ and phenyl.

8. The method of claim 1 wherein the compound m is 2, n is 1 and X is:

to give a group which is selected from:

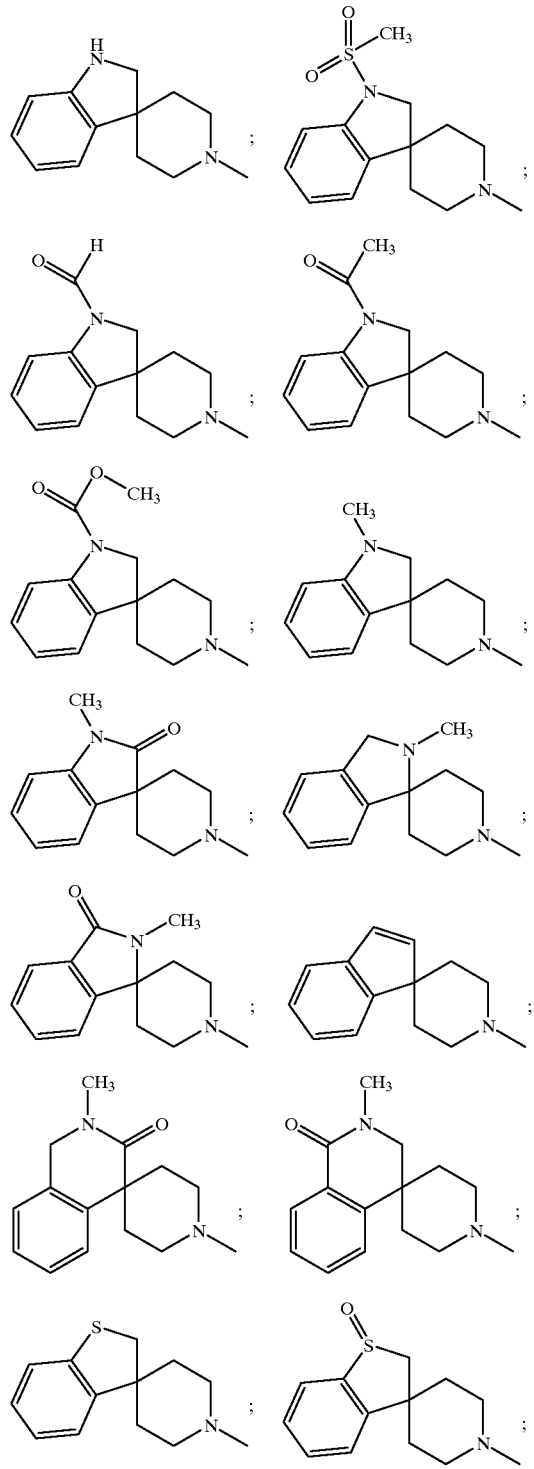

-continued

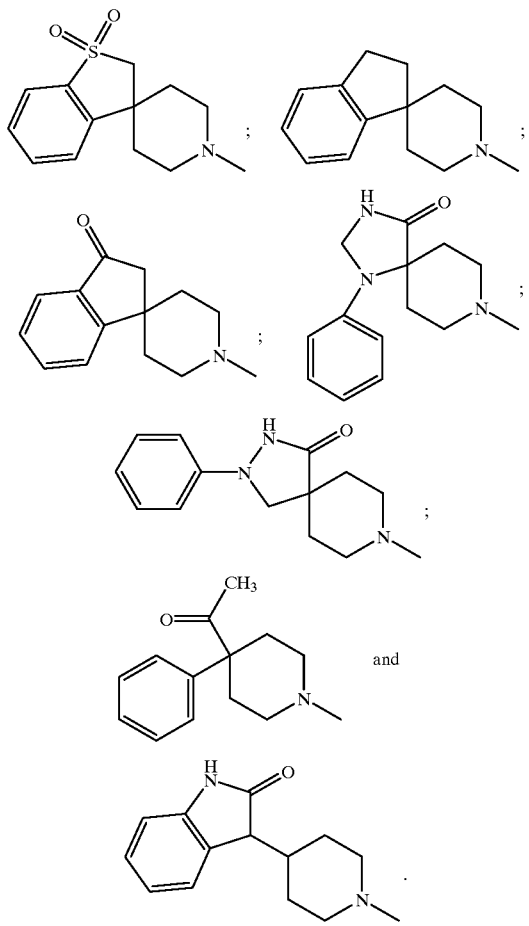

wherein each phenyl ring may be substituted by 1 or 2 substituents selected from:

hydroxy, cyano, —C(O)NR³R⁴, —NR³R⁴, —NR³COR⁴, halogen, trifluoromethyl, $C_{1-4}$alkyl, —S(O)$_p$$C_{1-4}$alkyl and —C(O)R³, where R³, R⁴ and p are as previously defined above.

9. The method of claim 1 wherein the compound m is 2, n is 1 and X is:

to give a group which is selected from:

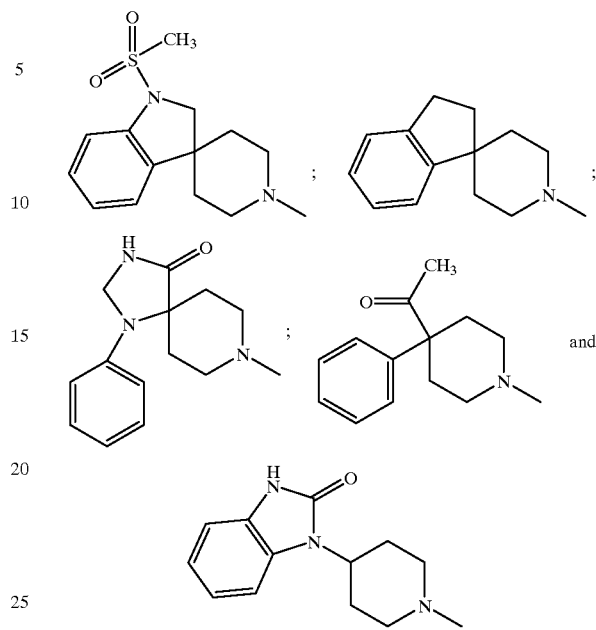

10. The method of claim 1 wherein the compound is selected from the group consisting of:

5-[3-{4,4-(N-sulfonamidomethyl-3,3-indolyl)piperidino}propyl]-5-[3,4-diphenyl]-1-benzylpiperidin-2-one;

5-[3-{4-(2-keto-1-benzimidazolinyl)-piperidino}propyl]-5-[3,4-dichlorophenyl]-1-benzylpiperidin-2-one;

5-[3-{4-acetyl-4-phenyl-piperidino}propyl]-5-[3,4-dichlorophenyl]-1-benzylpiperidin-2-one;

5-[3-{1-phenyl-1,3,8-triazaspiro[4.5]decan-4-one}propyl]-5-[3,4-dichlorophenyl]-1-benzylpiperidin-2-one;

5-[3-{4,4-(N-sulfonamidomethyl-3,3-indolyl)piperidino}propyl]-5-[3,4-diphenyl]-1-benzoylpiperidine;

5-[3-{4-(2-keto-1-benzimidazolinyl)-piperidino}propyl]-5-[3,4-dichlorophenyl]-1-benzoylpiperidine;

5-[3-{4-acetyl-4-phenyl-piperidino}propyl]-5-[3,4-dichlorophenyl]-1-benzoylpiperidine;

5-[3-{1-phenyl-1,3,8-triazaspiro[4.5]decan-4-one}propyl]-5-[3,4-dichlorophenyl]-1-benzoylpiperidine;

5-[3-{4,4-(1,1-indanyl)piperidino}propyl]-5-[3,4-diphenyl]-1-benzoylpiperidine; or a pharmaceutically acceptable salt thereof.

* * * * *